(12) United States Patent
Davis

(10) Patent No.: US 6,203,492 B1
(45) Date of Patent: Mar. 20, 2001

(54) SCOPE TESTER

(76) Inventor: James M. Davis, 4687 Pond Apple Dr. South, Naples, FL (US) 33999

(*) Notice: Subject to any disclaimer, the term of this patent is extended or adjusted under 35 U.S.C. 154(b) by 0 days.

(21) Appl. No.: 09/360,096

(22) Filed: Jul. 23, 1999

(51) Int. Cl.[7] ................................. A61B 1/00; A61B 1/06
(52) U.S. Cl. ..................... 600/101; 600/102; 600/160; 600/175; 385/117; 356/73.1
(58) Field of Search .................................. 600/101, 102, 600/160, 175; 385/116, 117; 356/73.1

(56) References Cited

U.S. PATENT DOCUMENTS

| | | | |
|---|---|---|---|
| 5,953,112 | * | 9/1999 | Rosow et al. ........................ 356/73.1 |
| 5,966,210 | * | 10/1999 | Rosow et al. ........................ 356/213 |

* cited by examiner

*Primary Examiner*—Linda C. M. Dvorak
*Assistant Examiner*—Jocelyn Debra Ram
(74) *Attorney, Agent, or Firm*—William E. Noonan

(57) ABSTRACT

A test apparatus is used in combination with a fiberoptic scope, which scope includes an eyepiece, an elongate scope body connected to and generally optically aligned with the eyepiece and a plurality of generally optically aligned lenses disposed within the scope body and optically communicating with the eyepiece. The apparatus includes a holder that supports the scope such that the eyepiece of the scope is exposed by the holder. A focusing member is telescopically interengaged with the holder. An inspection eyepiece assembly is mounted within the focusing member and includes an magnifying lens that faces and optically communicates with the eyepiece of a scope supported by the holder. The focusing member and the holder are telescopically adjusted relative to one another to focus the inspection eyepiece assembly on a selected lens of the scope. As a result, an image of the selected lens is transmitted through the inspection eyepiece assembly and examined. An assembly may also be used for magnifying, focusing and inspecting optical fibers of the scope.

14 Claims, 5 Drawing Sheets

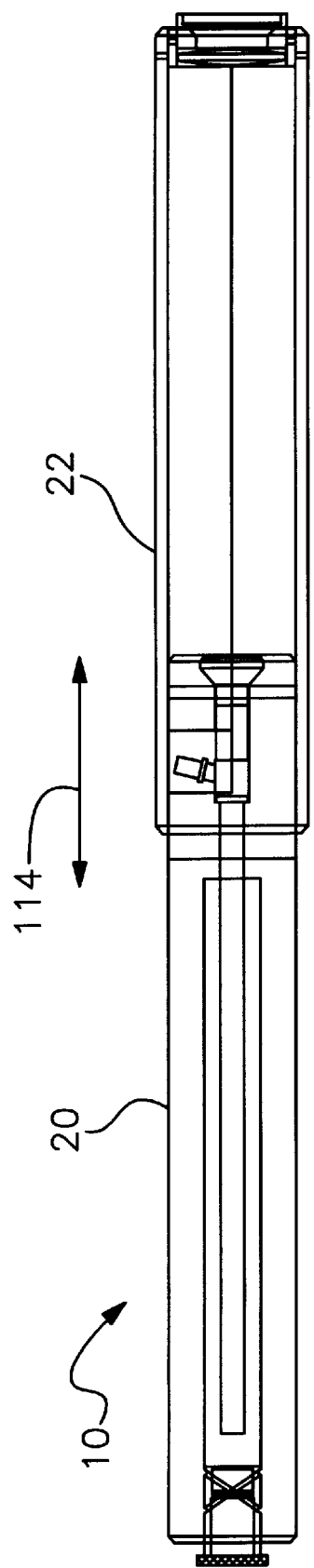
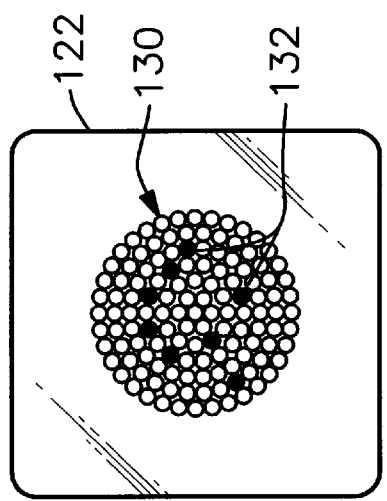
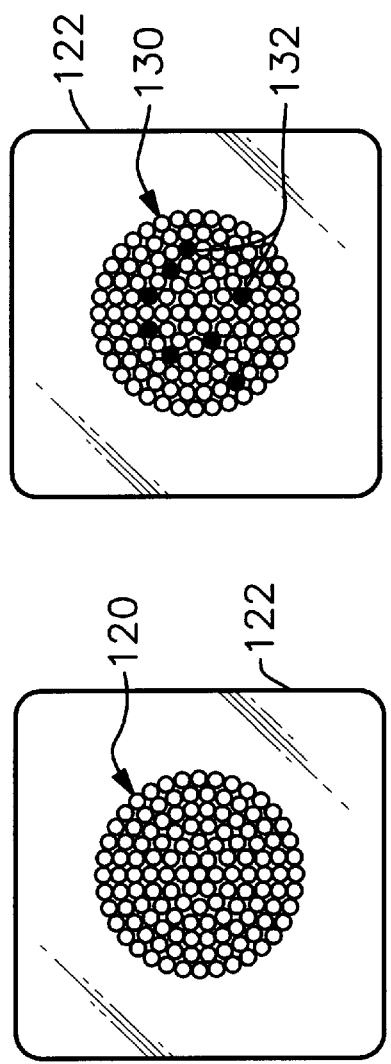
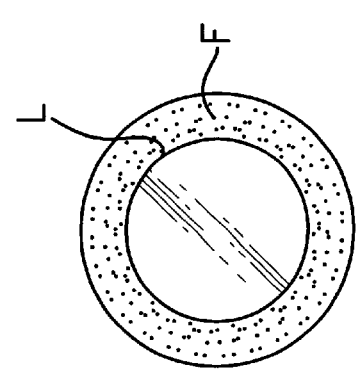

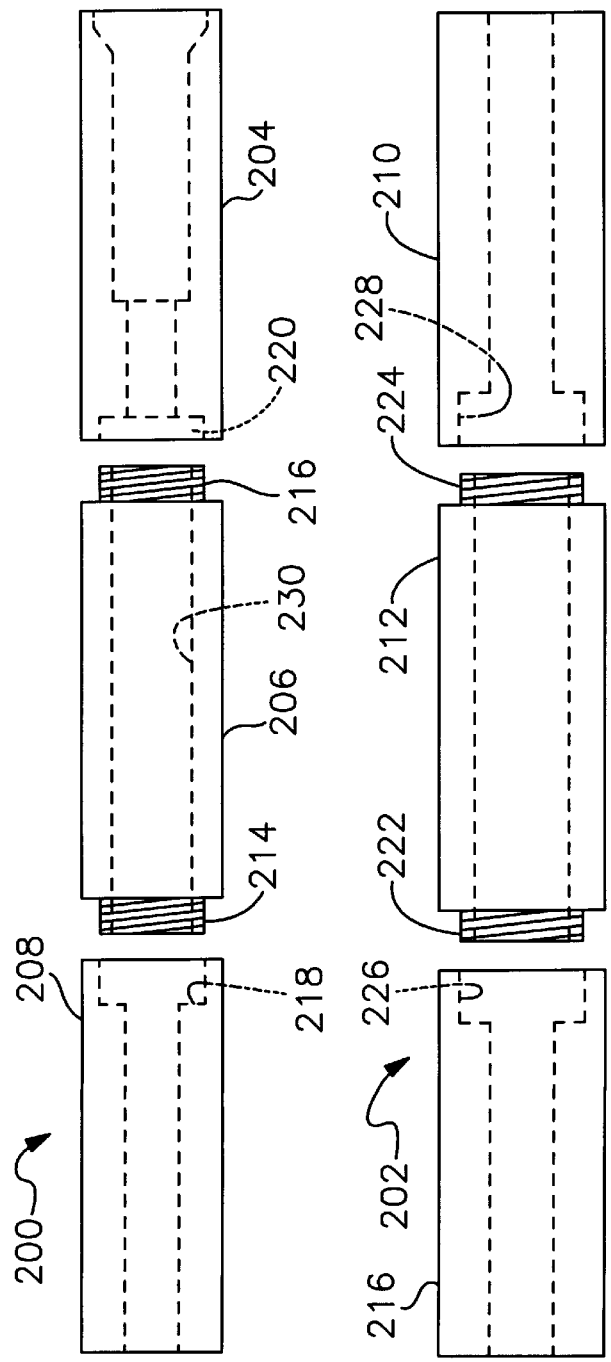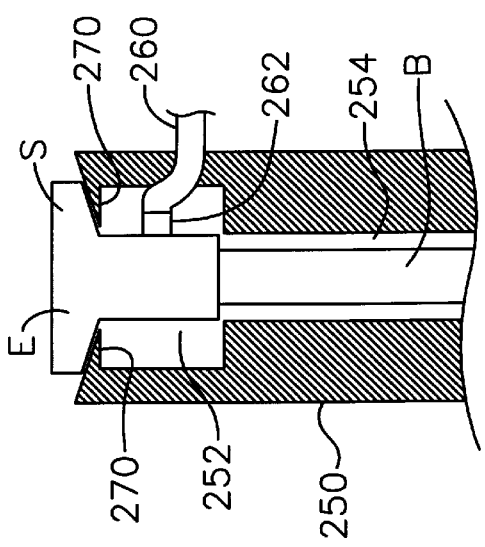

SCOPE TESTER

FIELD OF THE INVENTION

This invention relates to a device for testing scopes and, in particular, scopes that are used to perform medical and surgical procedures.

BACKGROUND OF THE INVENTION

Various lighted and unlighted scopes are presently available for conducting medical and surgical procedures. These include, for example, endoscopes, cystoscopes, arthroscopes, etc. Such scopes are extremely precise instruments that must be maintained in proper working condition. However, over time, most medical scopes tend to deteriorate and eventually exhibit problems. One or more of the lenses in the lens train are apt to become distorted or otherwise malfunction. Broken seals are also a common problem. Water droplets can collect on the lenses. Flexible scopes are particularly susceptible to lens damage. Constant flexing of the scope tends to bend, grind, crack and otherwise deform the lenses of the lens train. As a result, viewing through the scope is clouded or obscured. Typically such problems are discovered in the operating room or in other environments where the scope is being used. This can cause difficulties and delays in performing the required procedure. Currently there is no technique available for quickly, conveniently and inexpensively testing a scope between uses.

Most medical scopes are very expensive, typically costing thousands of dollars. Accordingly, a defective scope is normally tested and repaired, rather than discarded. To date, medical scopes are usually tested by first recording the view through the scope and then examining the scope lens by lens with a microscope to locate the defective lens or lenses. This requires that the scope and its lenses be disassembled, inspected, repaired and/or replaced. A large repair bill usually results. The cost for a hospital or other medical institution to maintain a number of scopes can be enormous.

The expense and difficulty of examining and repairing fiberoptic scopes is compounded because of the uncertainty and difficulty involved in locating the particular lens or lenses that are causing the problem. It is virtually impossible to accurately locate the precise defect without completely disassembling the scope and examine each individual lens. This is an incredibly time consuming and inefficient process that adds significantly to the cost of maintaining the scope.

A significant number of fiberoptic scopes also exhibit broken or otherwise defective fibers. Over time, the light transmitting fibers gradually weaken and eventually break. This is a particularly serious problem when flexible scopes are involved. Broken fibers cause the scope to transmit much less light. As a result, surgery and other medical procedures are poorly illuminated.

To date, the fibers of a medical scope have been tested primarily by "eye balling" the light output. This involves considerable guesswork and imprecision. Currently, there is no efficient tester available for quickly, accurately and conveniently testing both the lens train and the light carrying fibers of a medical scope.

SUMMARY OF THE INVENTION

It is therefore an object of this invention to provide a test apparatus for quickly, conveniently and accurately examining the lens train in a scope so that the source of an optical problem can be located by the user before the scope is put into use and before the scope is sent out for repairs.

It is a further object of this invention to provide a scope tester that permits both the lenses and the light carrying fibers of a scope to be examined in a quick, convenient and accurate manner so that repairs may be performed relatively quickly, efficiently and inexpensively.

It is a further object of this invention to provide a scope tester that is particularly effective for use with scopes used in the medical industry and which significantly improves the efficiency of procedures involving such scopes.

It is a further object of this invention to provide a fiberoptic scope tester that enables the user to determine the precise location of a defective lens in the scope before the scope is disassembled.

It is a further object of this invention to provide a fiberoptic scope tester that is operating room ready and that allows a defective scope to be found between uses of the scope so that delays and inefficiency are reduced.

It is a further object of this invention to provide a fiberoptic scope tester that is effective for use with virtually all types of scopes and which is particularly suited for use with flexible scopes.

This invention features a device for examining a scope of the type that includes an eyepiece, an elongate scope body connected to and generally optically aligned with the eyepiece and a plurality of generally optically aligned lens disposed within the scope body and optically communicating with the eyepiece. The scope examining device includes a holder that supports the scope such that the eyepiece of the scope is exposed by the holder. A focusing member is telescopically interengaged with the holder. An inspection eyepiece assembly is mounted in the focusing member. The inspection eyepiece assembly includes a magnifying lens that faces and optically communicates with the eyepiece of a scope supported by the holder. The focusing member and the holder are telescopically adjusted relative to one another to focus the magnifying lens of the inspection eyepiece assembly on a selected lens of the scope. As a result, an image of the selected lens is transmitted through the inspection eyepiece assembly and examined.

In a preferred embodiment, the holder and the focusing member comprise generally cylindrical elements. The holder and focusing member may be slidably interengaged. The holder may include a chamber that receives the scope. The chamber may have an open end that exposes to the inspection eyepiece the eyepiece of a scope received in the chamber. The holder may include a generally cylindrical holder body and a cap that is selectively disengaged from the holder body to introduce the scope into the chamber.

The focusing member may comprise a cylindrical element and the inspection eyepiece may include a viewing element having a viewing aperture formed therein and a lens holder attached to the viewing element and supporting the magnifying lens in generally optical alignment with the viewing aperture.

The scope examining device may further include a fiber testing assembly comprising a body having an inlet, an outlet and a passageway that transmits light from the inlet to the outlet. The fiber inspection body may be mounted telescopically to the holder such that the inlet faces a distal, light emitting portion of the body of a scope supported by the holder. The fiber testing assembly may further include a magnifying and focusing lens assembly mounted in the passageway. The fiber inspection body is telescopically adjusted relative to the holder such that light projected from the light emitting portion of the body of a scope supported by the holder is transmitted by the magnifying and focusing lens and emitted by the outlet of the fiber inspection body onto a target area. The body of the fiber testing assembly may be threadably interengaged with the holder and, more particularly, may be mounted in the chamber of the holder through an opening in the end of the holder opposite the open end that exposes the eyepiece of the scope. The body of the fiber testing assembly may be threadably interengaged with the holder. The body and the holder may have generally cylindrical configurations. One of the body and the holder may include a helical track and the other of the body and the holder may include bearing means for slidably interengaging the track to permit the body to the telescopically adjusted relative to the holder.

BRIEF DESCRIPTION OF THE DRAWINGS

Other objects, features and advantages will occur from the following description of a preferred embodiment and the accompanying drawings, in which:

FIG. 12 is an elevational, cross sectional view of the fully assembled scope tester in a telescopically expanded condition;

FIG. 13 is a plan view of a representative image transmitted through the inspection eyepiece assembly and, more particularly, the image of a selected lens of the scope being examined;

FIG. 14 is a perspective view of a target area on which an image is projected by the fiber testing assembly; the image indicates that the optical fibers of a scope engaged with the tester includes largely undamaged fibers and is in proper operating condition;

FIG. 15 is a view similar to FIG. 14 but disclosing a projected image from the tester which indicates that the fibers of an engaged scope are broken and the scope has deteriorated in condition such that it requires replacement;

FIG. 16 is an exploded side view of a multiple piece holder that may be used in the tester.

FIG. 17 is an exploded side view of a multiple piece focusing member that may be used in the tester; and FIG. 18 is a side, cross sectional view of an alternative slotted holder that may be used in the tester.

Figure 1:
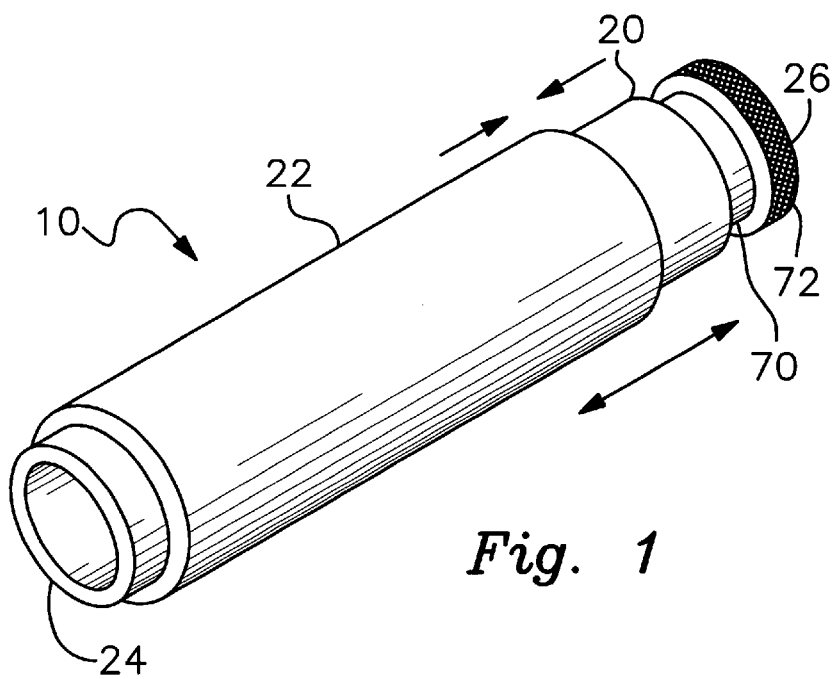
FIG. 1 is a preferred test device for examining scopes in accordance with this invention.

There is shown in FIG. 1 a test apparatus 10 for inspecting a fiberoptic scope. The scope that is inspected using the test apparatus of this invention typically comprises a fiberoptic scope of the type commonly employed in medical and surgical applications. Such scopes may include but are not limited to, endoscopes, gastroscopes, cystoscopes, esophogascopes, etc.

Figure 2:
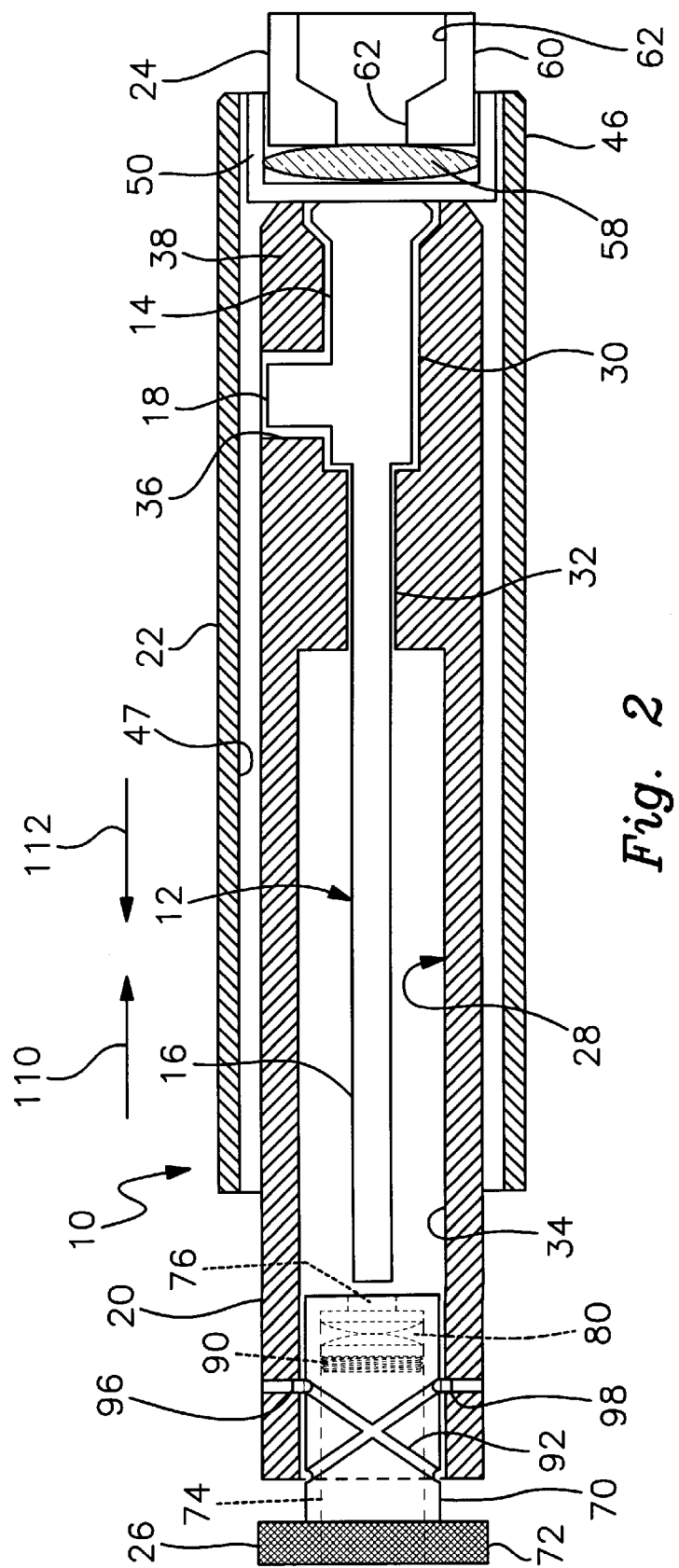
FIG. 2 is an elevational, partly cross sectional view of the scope tester.

As shown in FIG. 2, a representative scope 12 is supported by apparatus 10 so that the scope may be examined and tested. In the embodiment illustrated herein, the scope comprises an endoscope, although various other scopes may be tested in an analogous manner using apparatus 10. More particularly, scope 12 includes a standard (e.g. 55 mm or other standard size) eyepiece 14 and an elongate scope body 16 that is operably connected to and generally optically aligned with eyepiece 14. As will be known to those skilled in the art, a standard fiberoptic cable connection fitting 18 is attached and extends transversely from eyepiece portion 14. Multiple optical fibers and a lens train comprising a plurality of optically aligned lenses are mounted within scope body 16. These components are not specifically depicted in FIG. 2 but have a conventional construction. The elongate scope body 16 may be relatively rigid or flexible. During normal usage, eyepiece portion 14 is connected to a view camera and fitting 18 is connected to a light source through a fiberoptic cable. The distal end of body 16 includes a standard light emitting opening (not specifically shown). The elongate scope body is introduced into the human body to perform medical and surgical examinations in a known manner.

As shown in FIGS. 1 and 2, test apparatus 10 includes a pair of telescopically interconnected cylindrical parts, namely an interior holder 20 and an exterior focusing member 22. Holder 20 is longitudinally slidable within focusing member 22. An inspection eyepiece assembly 24 is mounted to focusing member 22 at one end of the apparatus. A fiber testing assembly 26 is telescopically interconnected to holder 20 at the opposite end of apparatus 10.

Figure 3:
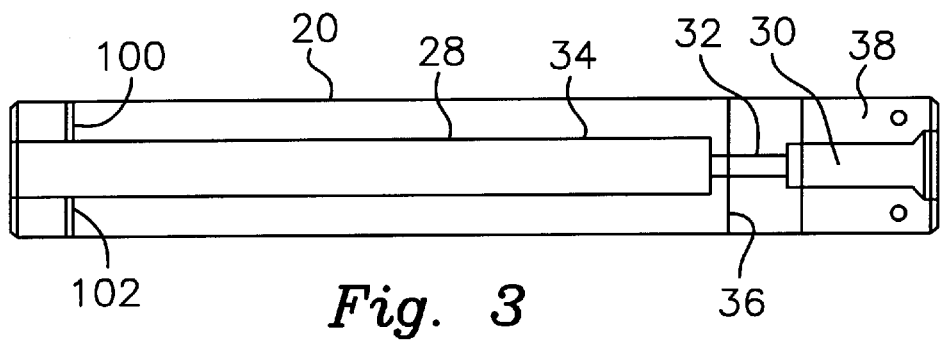
FIG. 3 is a top plan view of the scope holder component.

Holder 20, which is illustrated alone in FIG. 3, has a generally tubular configuration. A central chamber 28 is formed axially through holder 20. Chamber 28 includes, from right to left in FIGS. 2 and 3, an eyepiece receptacle 30, a narrow channel receptacle 32 and a wide channel receptacle 34. Eyepiece receptacle 30 accommodates eyepiece 14 of scope 12. The elongate body scope 16 extends through narrow and wide channel receptacles 32 and 34. A radial slot 36 is formed through the holder's body to accommodate scope fitting 18.

Figure 4:
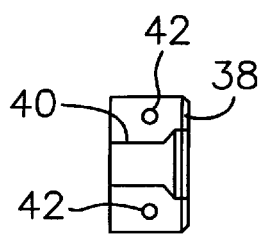
FIG. 4 is an elevational top view of the cap.
Figure 5:
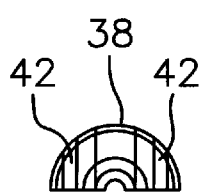
FIG. 5 is an elevational end view of the removable cap for the scope holder.
Figure 6:
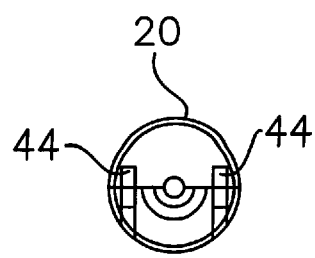
FIG. 6 is an elevational end view of the scope holder.

The right-hand end of holder 20 includes a removable cap 38, which is shown by itself in FIGS. 4 and 5. The inner surface of cap 38 includes an upper half 40 of eyepiece receptacle 30. The cap also includes a pair of connection holes 42 that are selectively engaged with corresponding pins 44, FIG. 6, carried by holder 20. Cap 38 is selectively removed from the remainder of holder 20 by disengaging holes 42 from pins 44 and lifting the cap upwardly. This permits scope 12 to be inserted into or removed from the holder as required.

Figure 7:
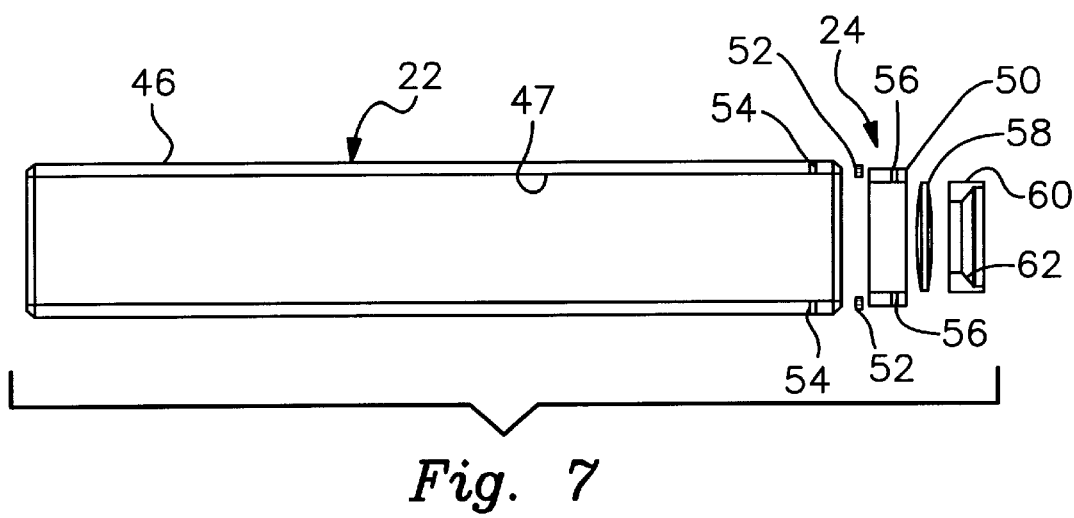
FIG. 7 is an elevational, cross sectional and exploded view of the focusing member and the inspection lens assembly.

Focusing member 22, FIGS. 1 and 2, is shown alone in FIG. 7. The focusing member comprises an elongate, tubular element 46 having an opening formed at each end. Tubular element 46 includes a central bore channel 47 that extends between the two ends of the tubular element. Inspection eyepiece assembly 24 is mounted to one end (in the illustrated version, the right-hand end) of tube 46. The inspection eyepiece assembly best shown in FIGS. 2 and 7, includes an annular lens holder 50 that is received within channel 47 of tubular element 46 proximate one end of the channel. The lens holder is secured within channel 47 such as by set screws 52 that are received through aligned holes 54 and 56 in tubular element 46 and holder 50, respectively.

A magnifying lens 58 is mounted adhesively or otherwise within the central opening of lens holder 50. An annular viewing element 60 having a central aperture 62 is likewise interengaged with lens holder 50 such that magnifying lens 58 is interposed between the lens holder and the aperture element. Lens 58 is optically aligned with aperture 62 and the axial opening through lens holder 50. When holder 20 is telescopically interengaged within focusing member 22, as shown in FIG. 2, axial chamber 28 in holder 20 is aligned with the axial opening in lens holder 50 and magnifying lens 58. As a result, when a scope 12 is disposed within axial chamber 28, the eyepiece 14 of the scope is optically aligned with magnifying lens 58 and aperture 62 of inspection eyepiece assembly 24. In this condition, the user is able to visually inspect the interior of scope 12 by viewing through aperture 62.

Figure 8:
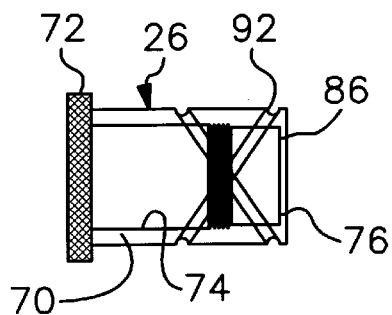
FIG. 8 is an elevational cross sectional view of the fiber testing assembly with the magnifying lenses omitted.

Fiber testing assembly 26, FIGS. 1 and 2, includes a generally cylindrical body 70 having a circumferentially knurled flange 72 formed at one end. As best shown in FIGS. 2 and 8, an axial passageway 74 is formed through body 70 and flange 72. A reduced diameter opening 76 is formed in the end of body 26 opposite the end that carries flange 72.

Figure 9:
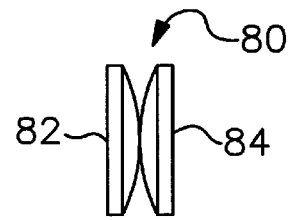
FIG. 9 is an elevational side view of the lenses used in the fiber testing assembly.
Figure 10:
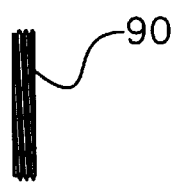
FIG. 10 is an elevational side view of the lens retainer utilized in the fiber testing assembly.
Figure 11:
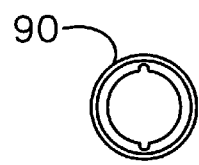
FIG. 11 is an elevational front view of the lens retainer.

As best represented in FIG. 2, a magnifying and focusing lens assembly 80 is mounted within central passageway 74 of fiber testing body 70. Lens assembly 80, shown alone in FIG. 9 comprises a pair of adjoining convex lens 82 and 84. In the embodiments shown herein, the convex surfaces of the lens face one another. It should be understood that various alternative lens assemblies and other magnifying and focusing assemblies may be utilized in accordance with this invention. The magnifying and focusing assembly may comprise various types and sizes of lens. Lenses having a diameter of approximately 20 mm and a focal length of 40 mm are particularly preferred. Alternative magnifications may be utilized. The particular magnification is chosen to correspond with the selected optical fibers being tested. Lens assembly 80 is installed within passageway 74 such that the lens assembly abuts a circumferential lip 86 (FIG. 8) formed at the forward end of body 70. The lens assembly is held in place by an annular locking ring 90, shown alone in FIGS. 10 and 11. Ring 90 has exterior threads formed on the circumferential surface thereof. These threads interengage complementary threads formed in the interior surface of body 70. When the ring is threaded in place within body 70, lens assembly 80 is held in place and axially and optically aligned within the passageway of body 70.

Assembly 26 is itself telescopically and adjustably interengaged within wide diameter receptacle 34 of chamber 28. As best shown in FIGS. 2 and 8, a helical track 92 is formed exteriorly on the tubular body 70 of assembly 26. Holder 20 carries an opposing pair of spring biased retainer bearings 96, 98 that are interengaged with helical track 92. As shown in FIG. 3, holder 20 includes a pair of radially opposed openings 100 and 102 that accommodate respective spring components for urging the bearings 96 and 98 radially inwardly into interengagement with track 92, in the manner depicted in FIG. 2. Such interengagement between the spring biased bearings and the helical track allows fiber testing assembly 26 to be telescopically adjusted relative to holder 20 by simply rotating assembly 26 in a selected direction. The user grasps knurled flange 72 and axially rotates assembly 26 to the right to advance body 70 within holder chamber 28. Alternatively, the user rotates assembly 26 axially to the left to retract body 70 from chamber 28. This enables the optical fibers of scope 12 to be inspected in the manner described more fully below. It should be understood that various other structures may be employed for telescopically interconnecting the fiber testing assembly to the holder. It should also be understood that in certain embodiments, the fiber testing assembly may be eliminated such that the apparatus of this invention is employed simply to examine the lens train.

To examine the lens train of a selected fiberoptic scope 12, holder 20 and focusing member 22 are pulled longitudinally apart and separated. Cap 38 is disengaged from holder 20 and scope 12 is installed in holder chamber 28 in the manner shown in FIG. 2. Focusing member 22 is then telescopically re-engaged with holder 20 in the manner shown in FIGS. 2 and 12 such that the holder and focusing member may be longitudinally adjusted between a retracted condition, shown in FIG. 2 and represented by opposing arrows 110 and 112, and an extended condition, shown in FIG. 12 and represented by doubleheaded arrow 114. With scope 12 received in chamber 28, the eyepiece 14 of the scope is optically aligned with inspection eyepiece 24. The user looks through aperture 62. This allows the user to view scope 12 internally through eyepiece 14. The user manually focuses the apparatus by sliding holder 20 and focusing member 22 between the positions illustrated in FIGS. 2 and 12. More particularly, the user focuses successively upon each lens of the lens train in scope body 16. The lens is inspected for cracks, stress, deformations, moisture and other defects. For example, as shown in FIG. 13, a user looking through inspection eyepiece 24 and longitudinally adjusting focusing 22 relative to holder 20 is able to focus upon an individual lens L. Optical fibers F of scope 12 appear peripherally about the focused lens L. The person inspecting the lens train can quickly and accurately determine whether the focused lens is in good condition or whether it is distorted or otherwise defective. If a defective lens is found, it can then be repaired quickly and cost effectively. The user/owner of the scope is able to accurately and efficiently examine the lens train and precisely determine the source of a problem before repairs are ordered. The scope owner can also then determine whether repair or replacement of the scope is truly required.

In order to analyze the condition of the optical fibers within the scope, holder 20 and focusing member 22 are pulled apart and separated from one another. The user then attaches a standard fiberoptic cable to fitting 18. The opposite end of the cable is attached to a suitable light source. The light source is then activated to transmit light through the cable. This light is transmitted through scope 12 and discharged from the distal end of scope body 16. The discharged light passes through opening 76 of assembly 20 and is transmitted through lens assembly 80. The light passes through passageway 74 and is discharged through the opening surrounded by flange 72. The user is able to magnify and focus the discharged light by grasping the exterior knurled surface of flange 26 and axially rotating assembly 26 within holder 20 in the manner previously described. Assembly 26 is longitudinally adjusted until a focused and magnified image is obtained. In FIG. 14, a sharp, enlarged image 120 is produced against a test target surface 122. An image that is clear and bright with relatively few dark spots indicates that few, if any individual fibers in the scope are broken. An unbroken individual fiber transmits light to the fiber testing assembly without interruption and the light from the fiber is projected onto target area 122. Conversely, if an individual fiber is broken, it will not transmit light and a corresponding black spot or dot will appear within the image. For example, in FIG. 15, an image 130 is projected onto target area 122. The image contains darkened regions 132 that correspond to and reveal numerous broken optical fibers that do not transmit light. When a large or substantial area of the projected contain such darkened regions, this indicates that the fibers of the scope are worn or deteriorated due to a corresponding number of broken fibers. As a result, the entire scope, or at least the fibers contained therein, should be replaced.

Accordingly, the lens train and/or optical fibers of a fiberoptic scope can be quickly and accurately examined by test apparatus 10. The holder 20 and focusing member 22 are longitudinally adjusted to allow the user to focus upon and inspect each lens in the lens train. Alternatively, the testing assembly 26 and the holder 20 are longitudinally adjusted so that light transmitted through the fibers of the scope may be focused and magnified a target area such that the condition of the fibers is revealed. The adjustability of the test apparatus permits clear images to be obtained for virtually all types of scopes and fibers. As a result, the test apparatus is extremely versatile and permits the condition of virtually any standard scope to be quickly and accurately checked when required. This enables, the scope to be maintained in proper working condition for medical, surgical and other applications. Repairs and/or replacement can be performed much more efficiently and cost effectively. The cause of poor scope performance is able to be ascertained almost immediately. The test apparatus thereby saves significant time and greatly improves efficiency, particularly in medical and dental environments where such benefits are quite important.

It should be understood that, in alternative embodiments, both lens and fiber testing may be performed using an apparatus similar to that previously described but without requiring a separate fiber testing assembly 26. For example, in cases where assembly 26 is eliminated, the lens train of scope 12 may be examined in the manner previously described. Following examination of the lens train, the scope is removed from and reversed within chamber 28. Scope body 16 is inserted through chamber 28 such that the distal, light emitting end of the scope body points toward inspection eyepiece assembly 24. Eyepiece 14 and fitting 18 are disposed outside of holder 20. The fiberoptic illuminator and cable are attached to fitting 18 and light is transmitted through the scope. The light is discharged from the scope and directed through inspection eyepiece assembly 24. Magnifying lens 58 magnifies the light projected from eyepiece assembly 24. The user telescopically and longitudinally adjusts focusing member 22 and holder 20 so that a projected image is provided onto a target area in a manner similar to that shown in FIGS. 14 and 15. As a result, the condition of the individual fibers can be quickly and accurately ascertained.

The components of apparatus 10, including the holder, the focusing tube and the fiber testing body are typically composed of durable plastics, metals or metal alloys. The lenses preferably comprise a lightweight plastic or glass composition.

As shown in FIGS. 16 and 17 an optional scope tester holder 200 and focusing member 202 may feature a multiple piece construction. In particular, holder 200 includes an eyepiece accommodating portion 204, intermediate portion 206 and a distal portion 208, which are axially aligned and releasably interconnected to one another. Similarly, focusing member 202 includes generally cylindrical portions 210, 212 and 216, which, once again, are axially aligned and releasably interconnected to one another. Intermediate portion 206 of holder 200 includes a pair of cylindrical threaded ends 214 and 216, which are threadably interengaged with complementary receptacles 218 and 220 in portions 208 and 204 respectively. Likewise, intermediate portion 212 of focusing member 202 includes exteriorly threaded ends 222 and 224 that are threadably interengaged with corresponding openings 226 and 228 formed in members 216 and 210 respectively.

Forming the holder and focusing member in multiple, interchangeable parts provides a number of advantages. For one thing, the axial opening formed through the holder assembly may be adjusted to accommodate scopes having varying scope body diameters. Some scopes may require a wider channel and others may require a narrower channel through the holder. For example, a desired diameter for an endoscope body is approximately 15 mm; whereas, a urology scope may require a diameter of only about 4 mm. The diameter of the channel 230 through the holder should be such that the scope body is held firmly in position within the holder and there is reasonably close optical alignment between the eyepiece and the lens train. The multiple part construction depicted in FIG. 16 permits the cylindrical portions of the holder to be interchanged so that a desired diameter is provided for channel 230. If the channel is too large, a piece 206 having a narrower diameter can be utilized.

As shown in FIG. 17, the focusing member may also employ a multiple part construction. Using multiple parts for the holder and the focusing member also permits holder and focusing member sections to be eliminated in certain applications. This permits the tester to employ a simpler and less expensive construction. A more compact, shorter tester can be used. In certain applications, there simply may be no need to use a tester and holder having the length shown above. A shorter, more compact and less awkward tester may be employed.

There is shown in FIG. 18 an optional holder 250 for a scope tester in accordance with this invention. Holder 250 again features an elongate, generally tubular or cylindrical construction. One end of holder 250 includes a countersunk slot 252 that is communicably connected to axial opening 254. A scope S is inserted into the holder through slot 252 such that eyepiece E is received within countersunk slot 252 and body B is received in axial channel 254. With the fiberoptic cable 260 removed from fitting 262, scope S fits conveniently into the slot and axial channel. The focusing member is then interengaged with the holder and operated in a manner similar to the previously described embodiment. This operation is not shown in FIG. 18, but is essentially the same as the procedure depicted above.

To test the optical fibers in scope S, the focusing member (not illustrated) is removed from holder 250. Fiberoptic cable 260 is attached to fitting 262 and eyepiece E is rotated until fitting 262 fits beneath and is held in place by a lip 270. As a result, the eyepiece and the scope S are held securely within holder 250. With the focusing member removed, as shown in FIG. 18, light is introduced through cable 262 into scope S. This light is transmitted through the fiberoptic cables in scope body B. As previously described, the light is emitted by the fiberoptic cables and transmitted through the optical fiber test assembly 26 shown above.

Employing the slotted opening allows the holder to be engineered and manufactured in a single piece. This eliminates the use of a separate cap or closure as described in the previous embodiment.

The tester that employs holder 250 thereby enables both the lens train and the optical fibers of the scope to be quickly and accurately tested. The lenses of the lens train are viewed and the optical fibers project light onto a target area in much the same way as previously described. In this version, the closure on the holder is eliminated and the eyepiece and scope body are inserted through the countersunk slot 252. Hose 260 extends outwardly out through the slot; therefore, the focusing member is removed from the holder before the optical fiber is tested.

It should be understood that the test apparatus may be modified within the scope of this invention to achieve the benefits and inventive principals disclosed herein.

Although specific features of the invention are shown in some drawings and not others, this is for convenience only as each feature may be combined with any or all of the features in accordance with the invention. Other embodiments, within the scope of this invention, will occur to those skilled in the art and are within the following claims:

What is claimed is:

1. A test apparatus for use in combination with a fiberoptic scope, which scope includes an eyepiece, an elongate scope body connected to and generally optically aligned with the eyepiece and a plurality of generally optically aligned lenses disposed within the body and optically communicating with the eyepiece, said apparatus comprising:

a holder that supports the scope such that the eyepiece of the scope is exposed by the holder;

a focusing member telescopically interengaged with said holder; and an inspection eyepiece assembly mounted in said focusing member and including a magnifying lens that faces and optically communicates with the eyepiece of a scope supported by said holder; said focusing member and said holder being telescopically adjusted relative to one another to focus said inspection eyepiece assembly on a selected lens of the scope, whereby an image of the selected lens is transmitted through said inspection eyepiece assembly and examined.

2. The apparatus of claim 1 in which said holder and said focusing member comprise generally cylindrical elements.

3. The apparatus of claim 1 in which said holder and said focusing member are slidably interengaged.

4. The apparatus of claim 1 in which said holder includes a chamber that receives said scope, said chamber having an open end for exposing the eyepiece of a scope received in the chamber to said inspection eyepiece.

5. The apparatus of claim 4 in which said holder includes a holder body and a cap that is selectively disengaged from said holder body to introduce the scope into said chamber.

6. The apparatus of claim 1 in which said focusing member comprises a cylindrical element and said inspection eyepiece assembly includes an aperture element having a viewing aperture formed therein and a lens holder attached to said aperture element and supporting said magnifying lens in optical alignment with said viewing aperture.

7. The apparatus of claim 1 further including a fiber testing assembly comprising a fiber inspection body having an inlet, an outlet and a passageway that transmits light from said inlet to said outlet, said body being telescopically mounted to said holder such that said inlet faces a distal light emitting portion of a scope body supported by said holder, said fiber testing assembly further including a magnifying and focusing lens assembly mounted in said passageway, said body being telescopically adjusted relative to said holder such that light projected from the light emitting portion of a scope body supported by said holder is transmitted by said magnifying and focusing lens and emitted by said outlet onto a target area.

8. The apparatus of claim 7 in which said body of said fiberoptic testing assembly is threadably interengaged with said holder.

9. The apparatus of claim 8 in which said body and said holder have generally cylindrical configurations.

10. The apparatus of claim 8 in which one of said body and such holder includes a helical track and the other of said body and said holder includes bearing means for slidably interengaging said track to permit said body to be telescopically adjusted relative to said holder.

11. The apparatus of claim 1 in which said holder and said focusing member each includes multiple releasably connected parts.

12. The apparatus of claim 1 in which said holder includes an axial slot formed proximate one end of said holder for receiving the eyepiece of the scope.

13. A test apparatus for use in combination with a fiberoptic scope, which scope includes a fitting that is interconnected to a fiberoptic conductor and through which light is introduced to the scope, a scope body having a light emitting portion and optical fibers disposed within the scope body, extending between the fiberoptic fitting and the light emitting portion and transmitting light from the fitting to the light emitting portion, which light is discharged from the scope body, said apparatus comprising:

a holder that supports the scope; and a fiber testing assembly that includes a body having an inlet, an outlet and a passageway that transmits light from said inlet to said outlet, said body being telescopically mounted to said holder such that said inlet faces the light emitting portion of a scope body supported by said holder, said fiber testing assembly further including a magnifying and focusing lens assembly mounted in said passageway, said body being telescopically adjusted relative to said holder such that light projected from the light emitting portion of a scope body supported by said holder is transmitted by said magnifying and focusing lens and emitted by said outlet onto a target area.

14. A test apparatus for use in combination with a fiberoptic scope, which scope includes an eyepiece, an elongate scope body connected to and generally optically aligned with the eyepiece, and a plurality of generally optically aligned lenses disposed within the body and optically communicating with the eyepiece, said a fitting communicably connected to at least one of the eyepiece and the scope body, which fitting is releasably interconnected to a fiberoptic conductor to introduce light into the scope, and the scope body having a light emitting portion and optical fibers disposed within the scope body and extending between the fiberoptic fitting and the light emitting portion and transmitting light from the fitting to the light emitting portion, which light is discharged from a scope body, said apparatus comprising:

a holder that supports the scope such that the eyepiece of the scope is exposed by the holder;

a focusing member telescopically interengaged with said holder;

an inspection eyepiece assembly mounted in said focusing member and including a magnifying lens that faces and optically communicates with the eyepiece of a scope supported by said holder; said focusing member and said holder being telescopically adjusted relative to one another to focus said inspection eyepiece assembly on a selected lens of the scope, whereby an image of the selected lens is transmitted through said inspection eyepiece assembly and examined; and a fiber testing assembly that includes a body having an inlet, an outlet and a passageway that transmits light from said inlet to said outlet, said body being telescopically mounted to said holder such that said inlet faces the light emitting portion of the scope body, said fiber testing assembly further including a magnifying and focusing lens assembly mounted in said passageway, said body being telescopically adjusted relative to said holder such that light projected from the light emitting portion of the scope body is transmitted by said magnifying and focusing lens and emitted by said outlet onto a target area.

* * * * *